(12) United States Patent
Lee

(10) Patent No.: US 10,750,962 B2
(45) Date of Patent: Aug. 25, 2020

(54) PULSE MEASUREMENT DEVICE AND COMPUTING DEVICE USING SAME

(71) Applicant: LG Innotek Co., Ltd., Seoul (KR)

(72) Inventor: Sang Hyun Lee, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 414 days.

(21) Appl. No.: 15/537,808

(22) PCT Filed: Dec. 15, 2015

(86) PCT No.: PCT/KR2015/013747
§ 371 (c)(1),
(2) Date: Jun. 19, 2017

(87) PCT Pub. No.: WO2016/099125
PCT Pub. Date: Jun. 23, 2016

(65) Prior Publication Data
US 2018/0271383 A1 Sep. 27, 2018

(30) Foreign Application Priority Data
Dec. 18, 2014 (KR) .......................... 10-2014-0183067

(51) Int. Cl.
*A61B 5/0245* (2006.01)
*A61B 5/0255* (2006.01)
(Continued)

(52) U.S. Cl.
CPC .......... *A61B 5/0245* (2013.01); *A61B 5/0059* (2013.01); *A61B 5/0255* (2013.01);
(Continued)

(58) Field of Classification Search
CPC ............ A61B 5/02; A61B 5/024–0255; A61B 5/02438; A61B 5/725; A61B 5/7225
See application file for complete search history.

(56) References Cited

U.S. PATENT DOCUMENTS 3,848,091 A * 11/1974 Stearns .................. H03G 9/025
73/585
3,886,469 A * 5/1975 Rollett .................. H03H 11/12
330/107
(Continued)

FOREIGN PATENT DOCUMENTS

JP 2003-290161 A 10/2003
JP 2004-121625 A 4/2004
(Continued)

OTHER PUBLICATIONS

Kuhn, K. (Jul. 26, 2009) Multistage Amplifiers. Retrieved from https://pdfs.semanticscholar.org/5294/6af073e453a42bf88d58a8554560c261b4fb.pdf (Year: 2009).*

(Continued)

*Primary Examiner* — Thaddeus B Cox
(74) *Attorney, Agent, or Firm* — Saliwanchik, Lloyd & Eisenschenk

(57) ABSTRACT

A pulse measurement device is provided, including: a pulse sensor that senses a user's pulse while in contact with the user's temple, and outputs the sensed result as a sensing signal; a signal processing unit that processes the sensing signal and outputs the processed result as a data signal; and a signal conversion unit that converts the data signal from an analogue form to a digital form and outputs the converted data signal as a pulse signal.

17 Claims, 8 Drawing Sheets

(51) Int. Cl.
   *A61B 5/024*   (2006.01)
   *A61B 5/00*    (2006.01)
   *G06F 3/01*    (2006.01)
   *G06F 3/041*   (2006.01)
   *G06F 3/16*    (2006.01)
   *G06F 1/16*    (2006.01)

(52) U.S. Cl.
   CPC ........ *A61B 5/02438* (2013.01); *A61B 5/6803* (2013.01); *A61B 5/725* (2013.01); *A61B 5/7225* (2013.01); *G06F 3/012* (2013.01); *G06F 3/041* (2013.01); *G06F 3/167* (2013.01); *A61B 5/742* (2013.01); *A61B 5/7405* (2013.01); *G06F 1/163* (2013.01)

(56) References Cited

U.S. PATENT DOCUMENTS

| | | | | |
|---|---|---|---|---|
| 3,978,849 | A * | 9/1976 | Geneen | A61B 5/024 600/503 |
| 4,275,453 | A * | 6/1981 | Wagner | H03H 11/1217 327/557 |
| 4,301,808 | A * | 11/1981 | Taus | A61B 5/024 600/500 |
| 4,396,890 | A * | 8/1983 | Kato | H03G 3/00 330/107 |
| 6,431,705 | B1 * | 8/2002 | Linden | G02C 11/00 351/158 |
| 6,491,647 | B1 * | 12/2002 | Bridger | A61B 5/021 128/900 |
| 6,783,501 | B2 * | 8/2004 | Takahashi | A61B 5/0059 600/479 |
| 7,217,244 | B2 * | 5/2007 | Suzuki | A61B 5/02444 600/481 |
| 7,543,934 | B2 * | 6/2009 | Howell | G01C 22/006 351/158 |
| 7,899,509 | B2 * | 3/2011 | Mannheimer | A41D 20/00 600/310 |
| 8,442,628 | B2 * | 5/2013 | Chang | H03F 3/45475 330/260 |
| 9,579,060 | B1 * | 2/2017 | Lisy | A61B 5/6803 |
| 10,052,030 | B2 * | 8/2018 | Abreu | A61B 5/01 |
| 10,265,019 | B2 * | 4/2019 | Gertsch | A61B 5/6803 |
| 2008/0159365 | A1 * | 7/2008 | Dubocanin | A61B 5/04004 375/219 |
| 2008/0171945 | A1 * | 7/2008 | Dotter | A61B 5/024 600/514 |
| 2012/0004519 | A1 | 1/2012 | Nazarian et al. | |
| 2012/0016245 | A1 * | 1/2012 | Niwa | A61B 5/02007 600/476 |
| 2012/0299870 | A1 * | 11/2012 | Chi | G02B 27/017 345/174 |
| 2015/0208933 | A1 * | 7/2015 | Satomi | A61B 5/02416 600/479 |
| 2018/0088355 | A1 * | 3/2018 | Blum | G02C 11/10 |

FOREIGN PATENT DOCUMENTS

| | | |
|---|---|---|
| KR | 10-2007-0084901 A | 8/2007 |
| KR | 10-2010-0097946 A | 9/2010 |
| KR | 10-2012-0070159 A | 6/2012 |
| KR | 10-2014-0066258 A | 5/2014 |

OTHER PUBLICATIONS

Build Your Own Heart Rate Monitor, Part 3 of 4: Hardware Design. (Aug. 22, 2012). Retrieved from http://www.ni.com/tutorial/14243/en/ (Year: 2012).*

Terrell, D. (1996). Op Amps: Design, Application, and Troubleshooting. Elsevier. (Year: 1996).*

International Search Report in International Application No. PCT/KR2015/013747, dated Dec. 15, 2015.

* cited by examiner

PULSE MEASUREMENT DEVICE AND COMPUTING DEVICE USING SAME

CROSS-REFERENCE TO RELATED APPLICATIONS

This application is the U.S. national stage application of International Patent Application No. PCT/KR2015/013747, filed Dec. 15, 2015, which claims priority to Korean Application No. 10-2014-0183067, filed Dec. 18, 2014, the disclosures of each of which are incorporated herein by reference in their entirety.

TECHNICAL FIELD

Embodiments relate to a pulse measurement device and a computing device using the same.

BACKGROUND ART

In modern society, coping with diseases such as adult diseases due to environmental problems and aging has become a major social challenge.

Pulse measurement is one of the simple health checkup methods, but provides essential and important biometric information. Therefore, there is growing demand for a method or device for more accurately and conveniently measuring a pulse.

In particular, for the elderly, the pulse rate may not be accurately measured when the pulse is measured at the wrist. Therefore, a device for measuring the pulse in a different manner is needed. Furthermore, it is also necessary to store the pulse data by measuring the pulse periodically for symptoms such as arrhythmia, which may occur at any time.

To this end, a variety of conventional pulse measurement devices for pulse measurement has been introduced. For example, conventional techniques for pulse measurement include a Korotkoff method and an optical sensor method.

Conventional pulse measurement devices employing the Korotkoff method are not only large in size but also incapable of immediately measuring the pulse while the devices are moved or when the user desires.

Conventional pulse measurement devices employing the optical sensor method emit light onto the blood using an optical sensor to sense the amount of blood flow and to measure the pulse using the amount of blood flow. However, when the pulse is measured in this manner, the pulse is irregularly measured and thus the accuracy is lowered. Moreover, since the optical sensor, which is essential for pulse measurement, protrudes to the outside, reliability of the optical sensor may be deteriorated due to fault of the optical sensor, which has low stiffness or waterproofness.

DISCLOSURE

Technical Problem

Embodiments provide a pulse measurement device and a computing device using the same which are compact and capable of measuring pulses from time to time and have excellent water resistance and stiffness.

Technical Solution

In one embodiment, a pulse measurement device may include a pulse sensor configured to sense a pulse in contact with a user's temple and to output a result of sensing as a sensing signal, a signal processing unit configured to process the sensing signal and to output a result of processing as a data signal, and a signal conversion unit configured to convert the data signal in an analog form into a digital form and output the converted digital signal as a pulse signal.

The pulse measurement device may further include an information notification unit configured to notify the pulse using the pulse signal.

The pulse sensor may include a piezoelectric sensor.

The signal processing unit may include a filter configured to filter a signal of a desired frequency band from the sensing signal, and an amplification unit configured to amplify the filtered signal and to output the amplified signal as the data signal.

The desired frequency band is 1 Hz to 1.5 Hz.

The filter may include a band pass filter configured to filter the signal of the desired frequency band.

The amplification unit may include a plurality of amplification stages.

A first amplification stage of the plurality of amplification stages may include a first operational amplifier, a first capacitor connected between a positive terminal of the first operational amplifier and the sensing signal, a first resistor connected between the positive terminal of the first operational amplifier and a reference potential, a second resistor connected between a negative terminal of the first operational amplifier and the reference potential, a second capacitor connected between the negative terminal and an output terminal of the first operational amplifier, and a third resistor connected in parallel with the second capacitor.

A second amplification stage of the plurality of amplification stages may include a second operational amplifier, a variable resistor connected between the output terminal of the first operational amplifier and the reference potential, a third capacitor connected between the variable resistor and a positive terminal of the second operational amplifier, a fourth resistor connected between the positive terminal of the second operational amplifier and the reference potential, a fifth resistor connected between a negative terminal of the second operational amplifier and the reference potential, a fourth capacitor connected between the negative terminal and an output terminal of the second operational amplifier, and a sixth resistor connected in parallel with the fourth capacitor.

A third amplification stage of the plurality of amplification stages may include a voltage follower connected between the output terminal of the second operational amplifier and the data signal.

The information notification unit may include at least one of a display unit configured to visually display the pulse, or a speaker configured to audibly notify the pulse.

In another embodiment, a computing device includes the pulse measurement device, a user interface unit configured to receive a command from the user and output a command signal, an optical device configured to generate a virtual image from the pulse signal and to displaying the generated virtual image to the user, and a computer configured to transmit, in response to the command signal, the pulse signal output from the pulse measurement device to an outside or the optical device wirelessly or by wire.

The computing device may further include a frame allowing the pulse measurement device, the user interface unit, the optical device, and the computer to be attached thereto, the frame having a shape wearable by the user.

The frame may be mounted on the user's ear.

The computing device may further include a rail attached to the frame, wherein the pulse sensor may slide on the rail and contact the temple.

The user interface unit may include a touch pad manipulated by the user to generate the command signal.

The user interface unit may include a microphone configured to generate the command signal using the user's voice.

The user interface unit may include a command sensing unit configured to sense movement of the computing device itself and to generate the command signal according to a result of sensing.

The frame may include a sensor area having a radius of curvature of a streamline convex toward the user, wherein the pulse sensor may be disposed in the sensor area.

Advantageous Effects

A pulse measurement device and a computing device using the same according to embodiments may measure the pulse more accurately than the conventional pulse measurement devices, and utilize a piezoelectric sensor which is superior to the optical sensor in terms of waterproofing and stiffness as compared with the conventional devices. Therefore, the devices according to the embodiments are highly reliable and are helpful in managing health of a user in real time in association with medical institutions. Further, the devices according to the embodiments may be easily mounted on wearable glasses or a head mounted display (HMD) as a compact and lightweight design is possible. Therefore, the devices according to the embodiments may enhance convenience and measure the pulse of the user from time to time to inform the user regardless of the surrounding environment.

BEST MODE

Figure 1:
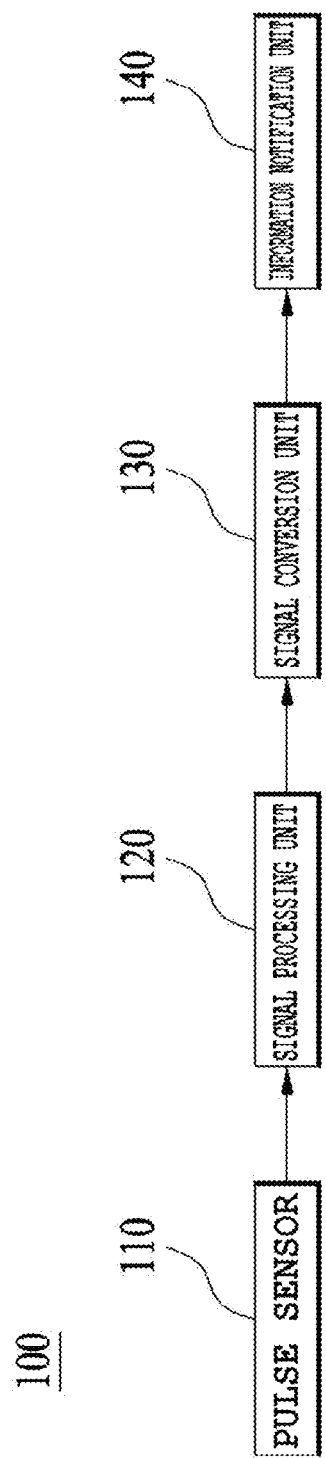
FIG. 1 is a schematic block diagram illustrating a pulse measurement device according to an embodiment.

Hereinafter, embodiments will be described in detail with reference to the accompanying drawings. However, the embodiments may be modified into various other forms, and the scope of the disclosure should not be construed as being limited to the embodiments described below. The embodiments are provided to enable those skilled in the art to more fully understand the present invention.

In the description of the embodiments, when an element is stated as being formed "on" or "under" another element, it can be directly "on" or "under" the other element or be indirectly formed with one or more elements disposed therebetween. When the term "on" or "under" is used, the meaning thereof may include not only the upper side but also lower side of one element.

It is also to be understood that the terms "first" and "second", "upper" and "lower" and the like used below do not require or imply any physical or logical relationship or order between such entities or elements, and may be used only to distinguish one entity or element from another entity or element.

The thickness and size of each layer in the drawings are exaggerated, omitted, or schematically shown for convenience and clarity of explanation. In addition, the size of each element does not entirely reflect the actual size.

FIG. 1 is a schematic block diagram illustrating a pulse measurement device 100 according to an embodiment, which may include a pulse sensor 110, a signal processing unit 120, a signal conversion unit 130, and an information notification unit 140.

The pulse sensor 110 may senses a pulse in contact with the user's (or a pulse measurement subject's) temple and output a sensed result to the signal processing unit 120 as a sensing signal. To this end, the pulse sensor 110 may be implemented as a piezoelectric sensor, but embodiments are not limited thereto. The piezoelectric sensor may contact the user's temple.

Figure 2:
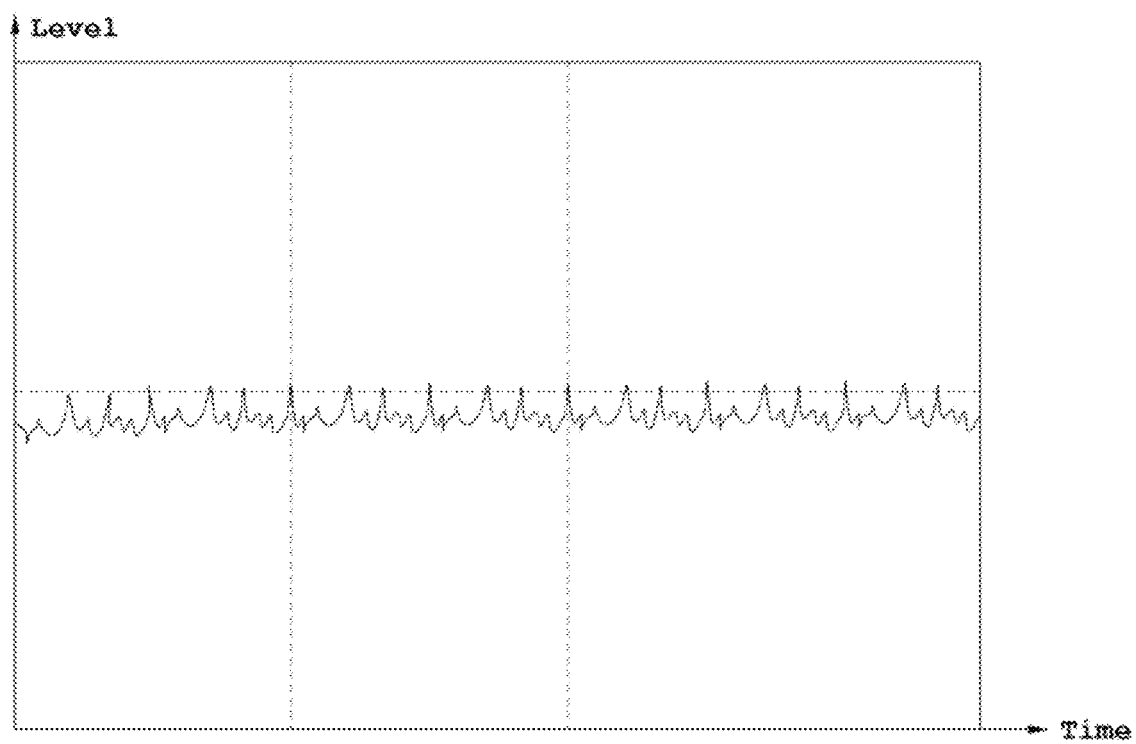
FIG. 2 is a graph depicting a sensing signal output from a pulse sensor.

FIG. 2 is a graph depicting a sensing signal output from the pulse sensor 110. The horizontal axis indicates time and the vertical axis indicates level.

In the case where the pulse sensor 110 is implemented as a piezoelectric sensor, the piezoelectric sensor may sense the user's pulse by contacting the user's temple and output the sensed result as a sensing signal to the signal processing unit 120, as illustrated in FIG. 2.

The signal processing unit 120 may process the sensing signal output from the pulse sensor 110 and output a result of signal processing as a data signal to the signal conversion unit 130.

Figure 3:
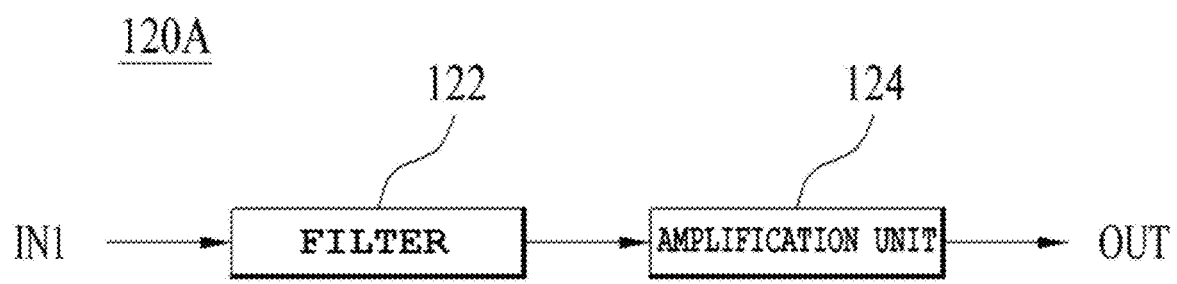
FIG. 3 is a block diagram illustrating an embodiment of a signal processing unit shown in FIG. 1.

FIG. 3 is a block diagram illustrating an embodiment 120A of the signal processing unit 120 shown in FIG. 1, which may include a filter 122 and an amplification unit 124.

The filter 122 may receive the sensing signal output from the pulse sensor 110 through an input terminal IN1, filter the signal of a desired frequency band from the sensing signal, and output the filtered result to the amplification unit 124. Here, the desired frequency band to be filtered by the filter 122 may be 1 Hz to 1.5 Hz, but embodiments are not limited thereto. The filter 122 may be implemented as a band pass filter (BPF), but embodiments are not limited thereto. That is, according to another embodiment, a signal of a desired frequency band may be filtered using a low pass filter (LPF) and a high pass filter (HPF) at the same time.

The amplification unit 124 amplifies the signal filtered by the filter 122 and outputs the amplified result to the signal conversion unit 130 through the output terminal OUT as a data signal. In some cases, the amplification section 124 may be omitted.

The level of the sensing signal output from the pulse sensor 110 may be very low as illustrated in FIG. 2. Accordingly, the amplification unit 124 may amplify the sensing signal having a low level. To this end, the amplification unit 124 may include a plurality of amplification stages.

Figure 4:
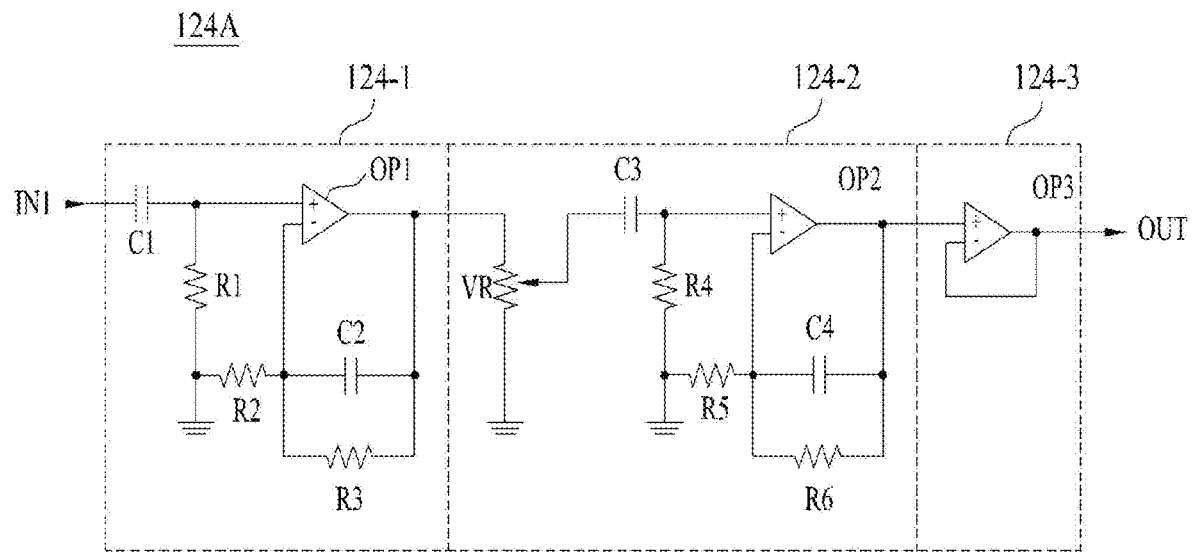
FIG. 4 is a circuit diagram illustrating an embodiment of an amplification unit shown in FIG. 3.

FIG. 4 is a circuit diagram illustrating an embodiment of the amplification unit 124 shown in FIG. 3, which may include a first amplification stage 124-1, a second amplification stage 124-2, and a third amplification stage 124-3.

The first amplification stage 124-1 may include a first operational amplifier OP1, first and second capacitors C1 and C2, and first to third resistors R1, R2 and R3.

The first capacitor C1 is connected between the positive terminal (+) of the first operational amplifier OP1 and the input terminal IN1, through which the sensing signal (that is, the signal filtered by the filter 122) is applied. The first resistor R1 is connected between the positive terminal (+) of the first operational amplifier OP1 and the reference potential (for example, ground). The second resistor R2 is connected between the negative terminal (−) of the first operational amplifier OP1 and the reference potential. The second capacitor C2 is connected between the negative terminal (−) of the first operational amplifier OP1 and the output terminal of the first operational amplifier OP1. The third resistor R3 is connected in parallel with the second capacitor C2.

The sensing signal output from the pulse sensor 110 and filtered by the filter 122 may be primarily amplified at the aforementioned first amplification stage 124-1.

In addition, the second amplification stage 124-2 may include a second operational amplifier OP2, a variable resistor VR, third and fourth capacitors C3 and C4, and fourth to sixth resistors R4, R5 and R6.

The variable resistor VR is connected between the output terminal of the first operational amplifier OP2 and the reference potential. The third capacitor C3 is connected between the variable resistor VR and the positive terminal (+) of the second operational amplifier OP2. The fourth resistor R4 is connected between the positive terminal (+) of the second operational amplifier OP1 and the reference potential. The fifth resistor R5 is connected between the negative terminal (−) of the second operational amplifier OP2 and the reference potential. The fourth capacitor C4 is connected between the negative terminal (−) of the second operational amplifier OP2 and the output terminal of the second operational amplifier OP2. The sixth resistor R6 is connected in parallel with the fourth capacitor C4.

The result of primary amplification at the first amplification stage 124-1 may be amplified secondarily at the second amplification stage 124-2 having the above-described configuration.

The third amplification stage 124-3 may include a voltage follower (or emitter follower) disposed between the second amplification stage 124-2 and the output terminal OUT. That is, the third amplification stage 124-3 may be connected between the output terminal of the second operational amplifier OP2 and the data signal.

For example, the voltage follower 126 may include a third operational amplifier OP3. The positive input terminal (+) of the third operational amplifier OP3 may be connected to the output of the second amplification stage 124-2, and the negative input terminal (−) and the output terminal of the third operational amplifier OP3 may be connected to each other.

Figure 5:
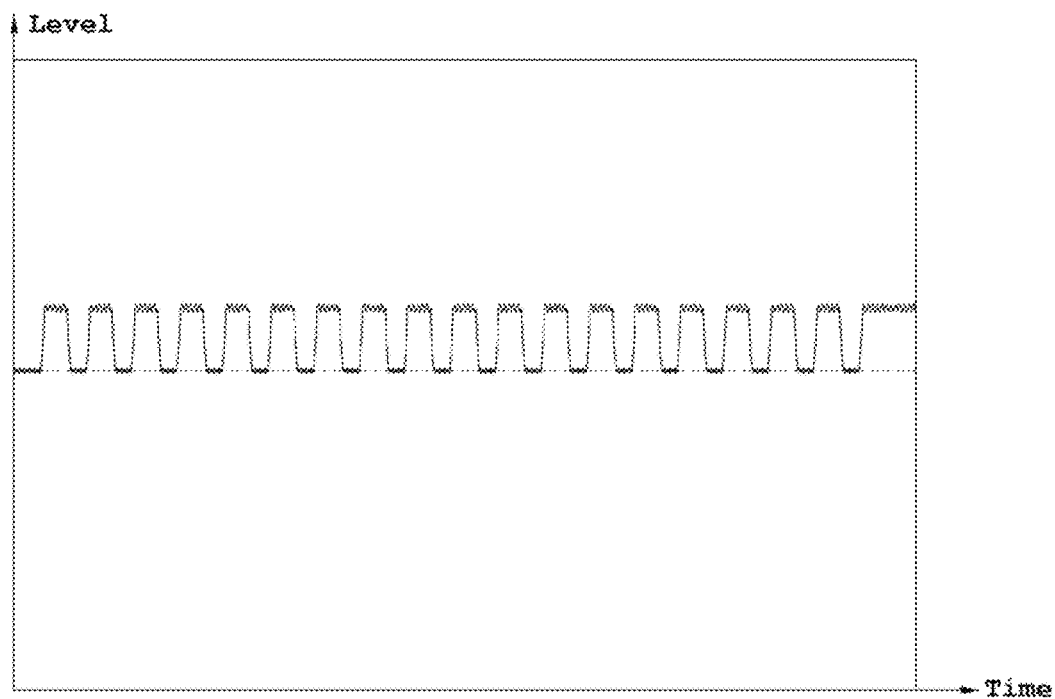
FIG. 5 is a waveform diagram of a pulse signal output from a signal conversion unit.

FIG. 5 is a waveform diagram of a pulse signal output from the signal conversion unit 130, wherein the horizontal axis indicates time, and the vertical axis indicates level.

The signal conversion unit 130 may convert an analog data signal output from the signal processing unit 120 into, for example, a digital signal as illustrated in FIG. 5, and output the converted digital pulse signal.

The information notification unit 140 may notify the user of the pulse of the user in various forms using the pulse signal output from the signal conversion unit 130.

Figure 6:
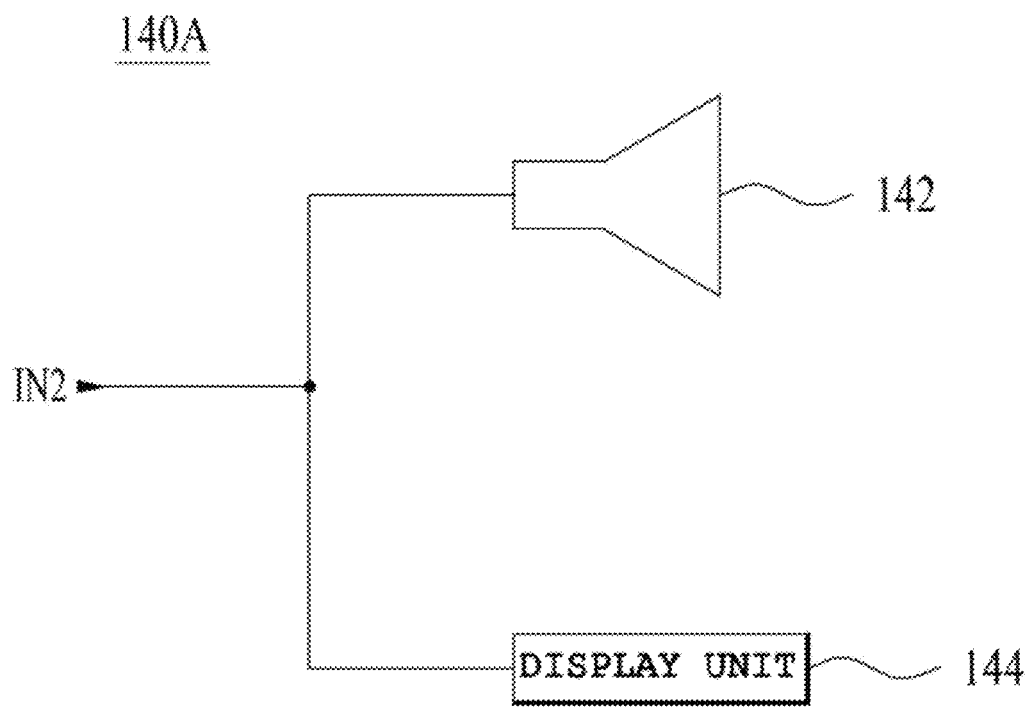
FIG. 6 is a block diagram according to an embodiment of an information notification unit shown in FIG. 1.

FIG. 6 is a block diagram according to an embodiment 140A of the information notification unit 140 shown in FIG. 1, which may include a speaker 142 and a display unit 144.

The speaker 142 may receive the pulse signal output from the signal conversion unit 130 through the input terminal IN2 and may audibly announce the user's pulse using the pulse signal. The display unit 144 may receive the pulse signal output from the signal conversion unit 130 through the input terminal IN2 and visually display the user's pulse using the pulse signal.

While FIG. 6 illustrates that the information notification unit 140A includes both the speaker 142 and the display unit 144, embodiments are not limited thereto. That is, according to another embodiment, the information notification unit 140A may include only the speaker 142 or only the display unit 144.

The above-described pulse measurement device 100 may be worn by the user in various ways. For example, the above-described pulse measurement device 100 may be mounted on a head mounted display (HMD), wearable glasses, or the like.

Figure 7:
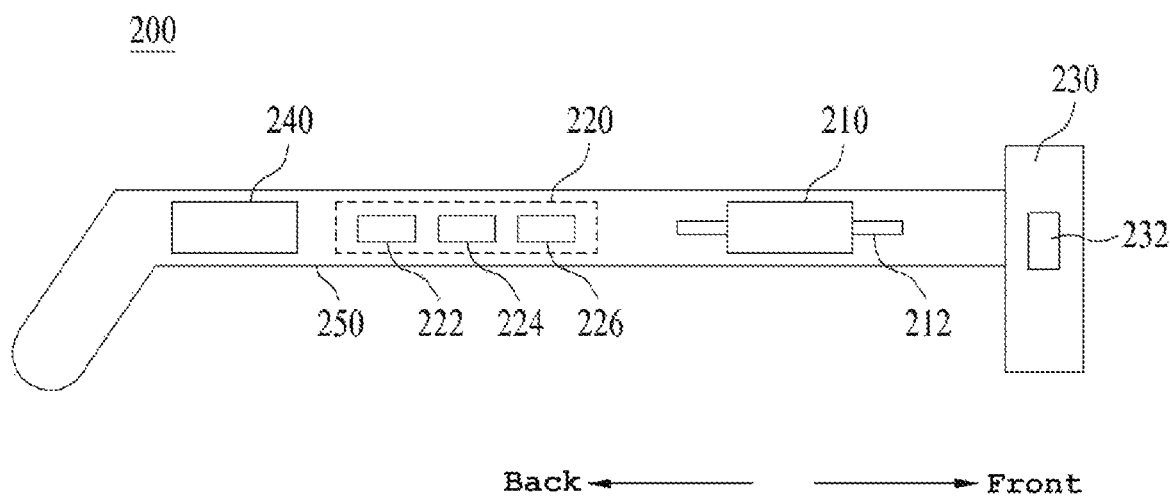
FIG. 7 schematically illustrates an external cross-sectional view of a computing device according to an embodiment.

FIG. 7 schematically illustrates an external cross-sectional view of a computing device 200 according to an embodiment.

The computing device 200 shown in FIG. 7 may include the pulse measurement device 210, a user interface unit 220, an optical device 230 including an image generation unit 232, a computer 240, and a frame 250.

The pulse measurement device 210 shown in FIG. 7 may correspond to the pulse measurement device 100 shown in FIG. 1. The pulse measurement device 100 shown in FIG. 7 may include the pulse sensor 110, the signal processing unit 120, and the signal conversion unit 130 excluding the information notification unit 140 in the pulse measurement device 100 of FIG. 1. In particular, in the pulse measurement device 210, the pulse sensor 110 may be arranged to contact the user's temple when the computing device 200 shown in FIG. 7 is worn by the user like eyeglasses. At this time, since the position of the temple may change according to the size of the face of the user, the pulse sensor 110 may slide along a rail 212 in the forward or backward direction indicated by arrows to contact the temple.

When the computer 240 functions as the signal processing unit 120 and the signal conversion unit 130 shown in FIG. 1, the pulse measurement device 210 shown in FIG. 7 may include only the pulse-sensor 110 shown in FIG. 1. In this case, the computer 240 may communicate with the pulse sensor 110 in a wired or wireless manner.

The user interface unit 220 may receive a command from the user, generate a command signal, and output the generated command signal to the computer 240. To this end, the user interface unit 220 may communicate with the computer 240 in a wired or wireless manner. For example, the user interface unit 220 may include at least one of a touch pad 222, a microphone 224, or a command sensing unit 226.

The user may provide the computer 240 with a command signal generated according to the result of operating the touch pad 222 or a command signal generated using the voice received through the microphone 224.

The command sensing unit 226 may include an accelerometer or a gyroscope, sense the motion of the computing device 200, and transmit a command signal generated according to the result of sensing to the computer 240.

Meanwhile, the image generation unit 232 of the optical device 230 may generate a virtual image from the pulse signal, and may display the generated virtual image to the user.

Figure 8:
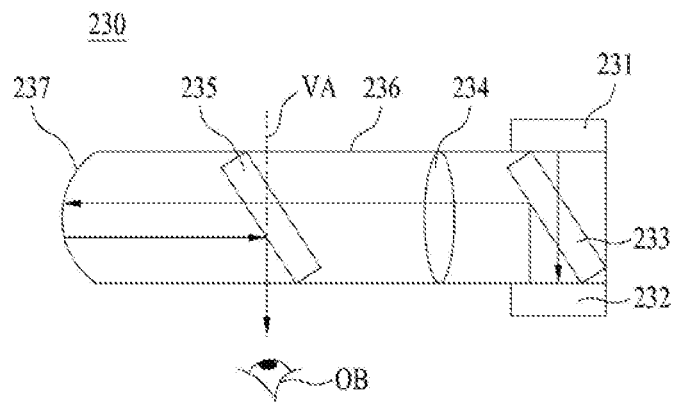
FIG. 8 schematically shows an example of an optical device shown in FIG. 7.

FIG. 8 schematically shows an example of the optical device 230 shown in FIG. 7.

The optical device 230 shown in FIG. 8 may include a light source 231, an image generation unit 232, a first beam splitting unit 233, a lens 234, a second beam splitting unit 235, and a light pipe 236.

The first beam splitting unit 233 projects light emitted from the light source 231, and the image generation unit 232 generates a light pattern corresponding to a virtual image using the light projected from the first beam splitting unit 23, and outputs light corresponding to the light pattern to the first beam splitting unit 233. At this time, the light emitted from the image generation unit 232 is reflected by the first beam splitting unit 233 and then emitted to the second beam splitting unit 235 through the lens 234. Thereafter, the second beam splitting unit 235 projects the light incident through the lens 234, and the light projected from the second beam splitting unit 235 is reflected by a reflection surface 237 of the light pipe 236 to form a virtual image. The light corresponding to the virtual image may be reflected by the second beam splitting unit 235 along the visual axis VA and viewed as the virtual image by the user OB.

The optical device 230 shown in FIG. 8 is merely an example, and embodiments are not limited thereto.

In response to a command signal output from the user interface unit 220 or stored as a default, the computer 240 may receive a pulse signal output from the pulse measurement device 210 and communicate with a computer (not shown) or other devices outside the computing device 200 in a wireless or wired manner.

In addition, the computer 240 may transmit the pulse signal output from the pulse measurement device 210 to the image generation unit 232. To this end, the computer 240 may exchange the pulse signal with the image generation unit 232 of the optical device 230 by wireless or wired communication.

In addition, the computer 240 may change or adjust the content of the pulse signal to be received from the pulse measurement device 210 and provided to the image generation unit 232, according to various types of command signals given from the user interface unit 220.

In addition, the pulse measurement device 210, the user interface unit 220, the optical device 230, and the computer 240 described above may be attached to the frame 250 as illustrated in FIG. 7. Here, the frame 250 may have a shape wearable by the user.

In addition, the above-described computing device 200 may not only provide the user with information on the pulse, but may also provide additional information such as a biorhythm.

Figure 9:
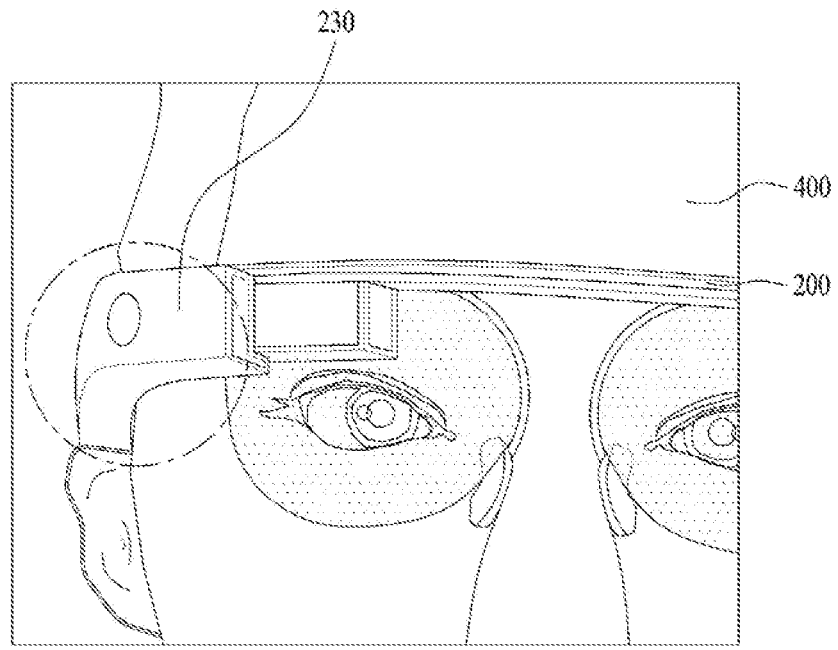
FIG. 9 shows an exemplary view of the computing device of FIG. 7 worn by a user.

FIG. 9 shows an exemplary view of the computing device 200 of FIG. 7 mounted to a user.

Referring to FIG. 9, the frame 250 of the computing device 200 according to the above-described embodiment may be mounted on an ear of the user 400.

Figure 10A:
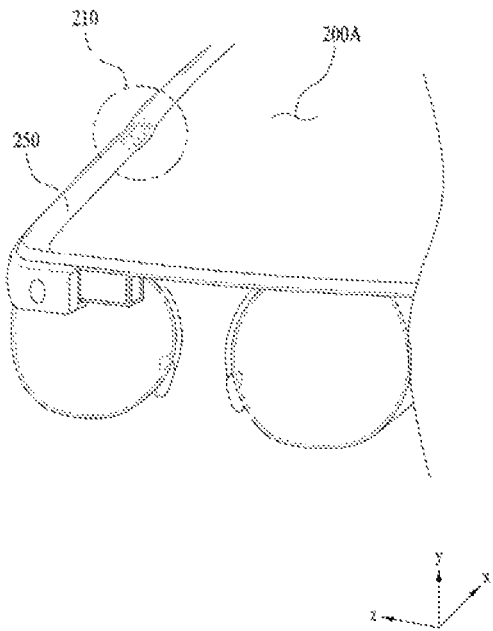
FIGS. 10a to 10c show perspective views of an embodiment of the computing device shown in FIGS. 7 and 9.
Figure 10B:
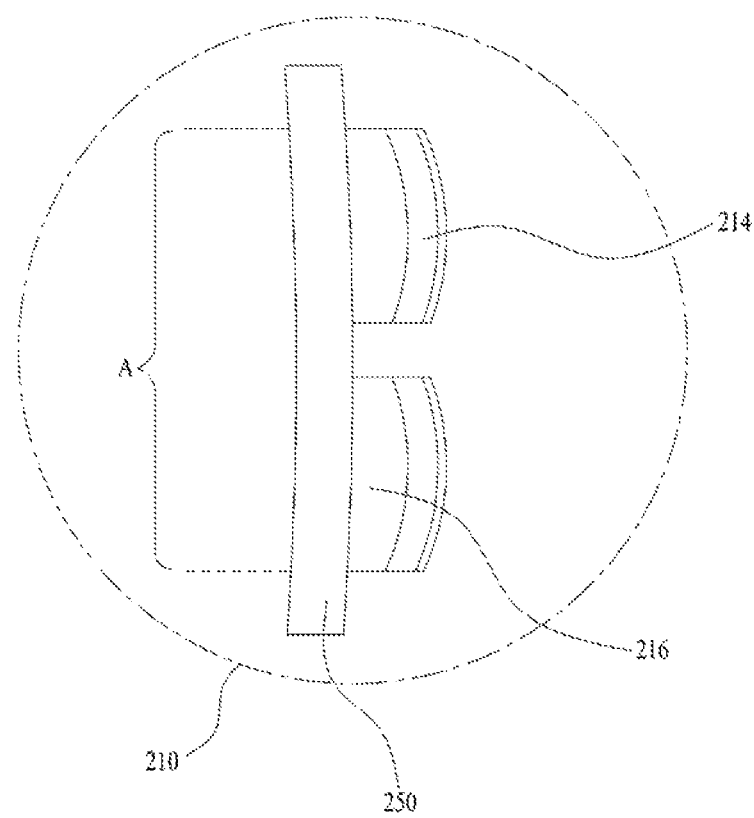
Figure 10C:
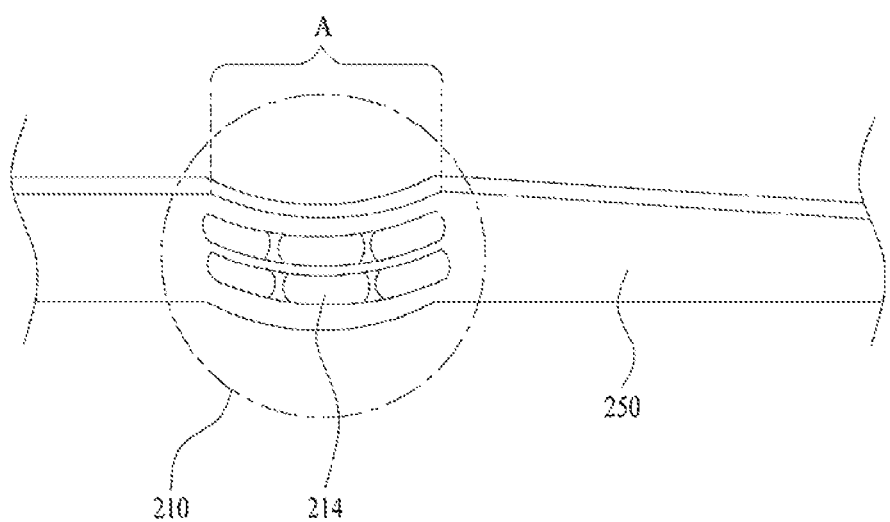

FIGS. 10a to 10c show perspective views of an embodiment 200A of the computing device 200 shown in FIGS. 7 and 9.

Referring to FIGS. 10a to 10c, the pulse sensor 110 in the pulse measurement device 210 may include a piezoelectric sensor 214 and a sensor capsule 216.

The pulse sensor 110 may be attached to a sensor area A of the frame 250. Unlike the other areas of the frame 250, the sensor area A may have a convex streamlined shape with a radius of curvature that is convex toward the user such that contact with the user's temple is ensured. The piezoelectric sensor 214 may be disposed in a film form to contact the user's temple.

The sensor capsule 216 may be disposed on the frame 250 and near the piezoelectric sensor 214. The sensor capsule 216 may be embodied as a thin elastic film of a silicone material for waterproofing or anti-contamination, but embodiments are not limited thereto.

As described above, the pulse measurement device 100, 210 according to an embodiment may measure the pulse more accurately than the pulse measurement device employing the conventional optical sensor method by sensing the pulse directly in contact with the temple of the user 400.

Particularly, when the pulse measurement device 100 according to an embodiment is applied to the computing device 200, 200A, the piezoelectric sensor 214 may be attached to the sensor area A of the streamlined frame 250, thereby more accurately sensing the pulse.

In addition, the pulse measurement device 100 according to an embodiment uses a piezoelectric sensor 110 which is superior to the optical sensor in terms of waterproofing and stiffness. For example, referring to FIG. 10b, the sensor capsule 216 may be used to further resist moisture or contamination. Therefore, high reliability of the device may be provided.

In addition, since the pulse measurement device 100 according to an embodiment may measure the pulse after being worn by the user 400 and communicate with an external agency, for example, a medical institution, through the computer 240, it may manage the health of the user 400 in real time in association with the medical institution. For example, the pulse measurement device 100 may transmit the pulse of the user 400 to the medical institution from time to time such that the emergency situation of the user 400 may be sensed in real time at the medical institution and the emergency rescue operation may be performed. Further, information about pulse measurements accumulated until an ambulance reaches the user may be provided to help treat the user 400.

Further, since the pulse measurement device 100 according to an embodiment uses the thin-film type piezoelectric sensor 110, it may be scaled down reduced in weight, thereby promoting convenience because the pulse measurement device 100 can be easily mounted on wearable glasses or an HMD.

Further, the pulse measurement device 100 according to an embodiment may be implemented as a wearable computing device 200 as illustrated in FIGS. 7 and 9, thereby measuring and providing the user's pulse at any time regardless of the surrounding environment.

While the present disclosure has been particularly shown and described with reference to exemplary embodiments thereof, it is to be understood that the disclosure is not limited to the embodiments. It will be understood by those skilled in the art that various modifications and applications which are not described above are possible without departing from the scope of the disclosure. For example, each component specifically shown in the embodiments may be modified and implemented. It is to be understood that all changes and modifications that come within the meaning and range of equivalency of the appended claims are therefore intended to be embraced therein.

MODE FOR INVENTION

The mode for carrying out the disclosure has been fully described in the "Best Mode".

INDUSTRIAL APPLICABILITY

The pulse measurement device according to embodiments may be applied to glasses or HMDs.

The invention claimed is:

1. A pulse measurement device comprising:
 a pulse sensor configured to sense a pulse when in contact with a user's temple and to output a result of sensing as a sensing signal;
 a signal processor configured to process the sensing signal and to output a result of processing as a data signal; and
 a signal converter configured to convert the data signal from an analog form to a digital form and output the converted digital signal as a pulse signal;
 wherein the signal processor comprises:
  a filter configured to filter a signal of a desired frequency band from the sensing signal; and
  an amplifying circuit configured to amplify the filtered signal and to output the amplified signal as the data signal,
  wherein the amplifying circuit comprises a plurality of amplification stages, a first amplification stage of the plurality of amplification stages comprising a first operational amplifier and a variable resistor directly connected with a first capacitor that is directly connected to a positive terminal of the first operational amplifier.

2. The pulse measurement device according to claim 1, comprising:
 an information transmitter configured to notify the user of the pulse based on the pulse signal.

3. The pulse measurement device according to claim 2, wherein the information transmitter comprises at least one of:
 a display configured to notify the user of the pulse by visual display; or
 a speaker configured to audibly notify the user of the pulse.

4. The pulse measurement device according to claim 1, wherein the pulse sensor comprises a piezoelectric sensor.

5. The pulse measurement device according to claim 1, wherein the desired frequency band is 1 Hz to 1.5 Hz.

6. The pulse measurement device according to claim 1, wherein the filter comprises:
 a band pass filter configured to filter the signal of the desired frequency band.

7. The pulse measurement device according to claim 1, wherein a second amplification stage of the plurality of amplification stages comprises:
 a second operational amplifier;
 a second capacitor connected between a positive terminal of the second operational amplifier and the sensing signal;
 a first resistor connected between the positive terminal of the second operational amplifier and a reference potential;
 a second resistor connected between a negative terminal of the second operational amplifier and the reference potential;
 a third capacitor connected between the negative terminal and an output terminal of the second operational amplifier; and
 a third resistor connected in parallel with the third capacitor.

8. The pulse measurement device according to claim 7, wherein the first amplification stage of the plurality of amplification stages comprises:
 a fourth resistor connected between the positive terminal of the first operational amplifier and the reference potential;
 a fifth resistor connected between a negative terminal of the first operational amplifier and the reference potential;
 a fourth capacitor connected between the negative terminal and an output terminal of the first operational amplifier; and
 a sixth resistor connected in parallel with the fourth capacitor.

9. The pulse measurement device according to claim 8, wherein a third amplification stage of the plurality of amplification stages comprises:
 a voltage follower connected between the output terminal of the first operational amplifier and the data signal.

10. A computing device comprising:
 the pulse measurement device according to claim 1,
 a user interface configured to receive a command from the user and output a command signal;
 an imaging device configured to generate a virtual image from the pulse signal and to displaying the generated virtual image to the user; and
 a computer configured to transmit, in response to the command signal, the pulse signal output from the pulse measurement device to an outside device or the imaging device either wirelessly or by wire.

11. The computing device according to claim 10, comprising:
 a frame allowing the pulse measurement device, the user interface, the imaging device, and the computer to be attached thereto, the frame having a shape wearable by the user.

12. The computing device according to claim 11, wherein the frame is configured to be mounted on the user's ear.

13. The computing device according to claim 11, comprising:
 a rail attached to the frame,
 wherein the pulse sensor slides on the rail and is capable of making contact with the temple.

14. The computing device according to claim 11, wherein the frame comprises a sensor area having a radius of curvature of a streamline configured to be convex toward the user,
 wherein the pulse sensor is disposed in the sensor area.

15. The computing device according to claim 10, wherein the user interface comprises a touch pad configured to be manipulated by the user to generate the command signal.

16. The computing device according to claim 10, wherein the user interface comprises a microphone configured to generate the command signal based on the user's voice.

17. The computing device according to claim 10, wherein the user interface comprises a command sensor configured to sense movement of the computing device itself and to generate the command signal according to a result of sensing.

* * * * *